(12) United States Patent
Smart

(10) Patent No.: US 7,207,334 B2
(45) Date of Patent: *Apr. 24, 2007

(54) RESPIRATORY MASK ASSEMBLY

(75) Inventor: Gregory S. Smart, Randwick (AU)

(73) Assignee: ResMed Limited, North Ryde (AU)

( * ) Notice: Subject to any disclaimer, the term of this patent is extended or adjusted under 35 U.S.C. 154(b) by 573 days.

This patent is subject to a terminal disclaimer.

(21) Appl. No.: 10/164,370

(22) Filed: Jun. 10, 2002

(65) Prior Publication Data

US 2002/0153012 A1 Oct. 24, 2002

Related U.S. Application Data

(62) Division of application No. 09/498,705, filed on Feb. 7, 2000, now Pat. No. 6,491,034.

(30) Foreign Application Priority Data

Feb. 9, 1999 (AU) .................... PP8550

(51) Int. Cl.
*A62B 18/08* (2006.01)

(52) U.S. Cl. .......... 128/206.24; 128/206.26; 128/206.21; 128/202.27

(58) Field of Classification Search ........... 128/206.24, 128/206.26, 204.18, 202.27, 206.12, 206.21
See application file for complete search history.

(56) References Cited

U.S. PATENT DOCUMENTS

| | | | |
|---|---|---|---|
| 35,724 A | 6/1862 | Wilcox | |
| 463,351 A | 11/1891 | Elliott | |
| 715,611 A | 12/1902 | Schenker et al. | |
| 716,530 A | 12/1902 | Giddens | |
| 812,706 A | 2/1906 | Warbasse | |
| 1,333,075 A | 3/1920 | Hill et al. | |
| 1,381,826 A | 6/1921 | Hansen | |
| 1,672,165 A | 6/1928 | Lewis | |
| 1,733,020 A | 10/1929 | Jones | |
| 2,029,129 A | 1/1936 | Schwartz | |
| 2,033,448 A | 3/1936 | James | |
| 2,141,222 A | 12/1938 | Pioch | |
| 2,359,506 A | 10/1944 | Battley et al. | |

(Continued)

FOREIGN PATENT DOCUMENTS

DE 297 21 766 U1 3/1998

(Continued)

OTHER PUBLICATIONS

Japanese Office Action English Translation for JP 2000-029094, 3 pages.

(Continued)

*Primary Examiner*—Mital Patel
(74) *Attorney, Agent, or Firm*—Nixon & Vanderhye P.C.

(57) ABSTRACT

A respiratory mask assembly for delivering breathable gas to a patient includes a mask frame having a first cooperating interlocking structure. A cushion clip having a second cooperating interlocking structure is selectively detachable to the mask frame. The first and second cooperating interlocking structures interlock with one another in a cooperating relationship to secure the cushion clip on the mask frame. A mask cushion has a portion positioned between the mask frame and the cushion clip so as to retain the mask cushion on the mask frame.

21 Claims, 3 Drawing Sheets

U.S. PATENT DOCUMENTS

| | | | |
|---|---|---|---|
| 2,371,965 | A | 3/1945 | Lehmberg |
| 2,454,103 | A | 11/1948 | Swidersky |
| 2,638,161 | A | 5/1953 | Jones |
| 2,823,671 | A * | 2/1958 | Garelick ............... 128/206.15 |
| 2,832,015 | A | 4/1958 | Ortega |
| 2,893,387 | A | 7/1959 | Gongoll et al. |
| 3,141,213 | A | 7/1964 | Nicholas |
| 3,189,027 | A | 6/1965 | Bartlett, Jr. |
| 3,474,783 | A | 10/1969 | Ulmann |
| 3,494,072 | A | 2/1970 | Olson |
| 3,523,534 | A | 8/1970 | Nolan |
| 3,535,810 | A | 10/1970 | Baehrle |
| 3,555,752 | A | 1/1971 | Bogaert |
| 3,824,999 | A | 7/1974 | King |
| 4,049,357 | A | 9/1977 | Hamisch, Jr. |
| 4,064,875 | A | 12/1977 | Cramer et al. |
| 4,111,197 | A | 9/1978 | Warncke et al. |
| 4,121,580 | A | 10/1978 | Fabish |
| 4,164,942 | A | 8/1979 | Beard et al. |
| 4,226,234 | A | 10/1980 | Gunderson |
| 4,274,404 | A | 6/1981 | Molzan et al. |
| 4,380,102 | A | 4/1983 | Hansson |
| 4,494,538 | A | 1/1985 | Ansite |
| 4,506,665 | A | 3/1985 | Andrews et al. |
| 4,549,334 | A | 10/1985 | Miller |
| 4,580,556 | A | 4/1986 | Kondur |
| 4,606,340 | A | 8/1986 | Ansite |
| 4,622,964 | A | 11/1986 | Flynn |
| 4,633,972 | A | 1/1987 | DeRocher |
| 4,783,029 | A | 11/1988 | Geppert et al. |
| 4,794,921 | A | 1/1989 | Lindkvist |
| 4,807,617 | A | 2/1989 | Nesti |
| 4,809,692 | A | 3/1989 | Nowacki et al. |
| 4,835,820 | A | 6/1989 | Robbins, III |
| 4,841,953 | A | 6/1989 | Dodrill |
| 4,870,963 | A | 10/1989 | Carter |
| 4,875,714 | A | 10/1989 | Lee |
| 4,898,174 | A | 2/1990 | Fangrow, Jr. |
| 4,899,614 | A | 2/1990 | Kataumi |
| 4,974,586 | A | 12/1990 | Wandel et al. |
| 4,997,217 | A | 3/1991 | Kunze |
| 5,005,568 | A | 4/1991 | Loescher et al. |
| 5,136,760 | A | 8/1992 | Sano et al. |
| 5,215,336 | A | 6/1993 | Worthing |
| 5,243,971 | A | 9/1993 | Sullivan et al. |
| 5,253,641 | A * | 10/1993 | Choate .................. 128/200.14 |
| 5,311,862 | A | 5/1994 | Blasdell et al. |
| 5,398,673 | A | 3/1995 | Lambert |
| 5,438,981 | A | 8/1995 | Starr et al. |
| 5,501,214 | A | 3/1996 | Sabo |
| 5,645,049 | A | 7/1997 | Foley et al. |
| 5,647,355 | A | 7/1997 | Starr et al. |
| 5,676,133 | A * | 10/1997 | Hickle et al. .......... 128/205.12 |
| 5,709,204 | A | 1/1998 | Lester |
| 5,724,965 | A * | 3/1998 | Handke et al. ........ 128/207.13 |
| 5,839,436 | A | 11/1998 | Fangrow et al. |
| 5,860,677 | A | 1/1999 | Martins et al. |
| 5,896,857 | A | 4/1999 | Hely et al. |
| 5,937,851 | A | 8/1999 | Serowski et al. |
| 5,979,025 | A | 11/1999 | Horng |
| 6,082,360 | A | 7/2000 | Rudolph et al. |
| 6,189,532 | B1 | 2/2001 | Hely et al. |
| 6,192,886 | B1 | 2/2001 | Rudolph |
| 6,196,223 | B1 * | 3/2001 | Belfer et al. ........... 128/206.25 |
| 6,240,605 | B1 | 6/2001 | Stevens et al. |
| 6,250,375 | B1 | 6/2001 | Lee et al. |
| 6,256,846 | B1 | 7/2001 | Lee |
| 6,272,722 | B1 | 8/2001 | Lai |
| 6,321,421 | B1 | 11/2001 | Lim |
| 6,381,813 | B1 | 5/2002 | Lai |
| 6,412,487 | B1 * | 7/2002 | Gunaratnam et al. .. 128/206.24 |
| 6,449,817 | B1 | 9/2002 | Hsu |
| 6,463,931 | B1 | 10/2002 | Kwok et al. |
| 6,491,034 | B1 | 12/2002 | Gunaratnam et al. |
| 6,513,206 | B1 | 2/2003 | Banitt et al. |
| 6,520,182 | B1 | 2/2003 | Gunaratnam |
| 6,532,961 | B1 | 3/2003 | Kwok et al. |
| 6,615,832 | B1 * | 9/2003 | Chen .................... 128/206.26 |
| 6,796,308 | B2 | 9/2004 | Gunaratnam et al. |
| 2002/0174868 | A1 | 11/2002 | Kwok et al. |
| 2003/0005935 | A1 | 1/2003 | Kwok et al. |
| 2004/0134497 | A1 | 7/2004 | Gunaratnam et al. |

FOREIGN PATENT DOCUMENTS

| | | | |
|---|---|---|---|
| EP | 1 027 905 A3 | | 8/2000 |
| FR | 2 691 906 | | 12/1993 |
| JP | 48-55696 | | 10/1971 |
| JP | 59-55535 | | 4/1984 |
| JP | 61-67747/86 | | 5/1986 |
| JP | 7-21058/95 | | 4/1995 |
| JP | 7-308381 | | 11/1995 |
| JP | 9-501084 | | 2/1997 |
| WO | WO 80/01645 | | 8/1980 |
| WO | WO 87/01950 | * | 4/1987 |
| WO | WO 95/04566 | | 2/1995 |
| WO | WO 98/26830 | | 6/1998 |
| WO | WO 98/48878 | | 11/1998 |
| WO | WO 99/30760 | | 6/1999 |
| WO | WO 00/38772 | | 7/2000 |

OTHER PUBLICATIONS

ResCare Limited, "Sullivan™ Nasal CPAP System, *Nose Mask Clip—User Instructions*" May 1990, 1 page.
U.S. Appl. No. 10/123,484, filed Apr. 17, 2002, Gunaratnam et al.
ResMed, Mask Systems Product Brochure, 2 pages, Sep. 1992.
Respironics, Inc. "Nasal Mask System Silicon Contour Mask" Product Instructions, 2 pages, Jun. 1997.
U.S. Appl. No. 09/985,458, filed Nov. 2, 2001, Gunaratnam et al.
U.S. Appl. No. 09/985,457, filed Nov. 2, 2001, Gunaratnam et al.
U.S. Appl. No. 09/501,004, filed Feb. 9, 2000, Gunaratnam.
U.S. Appl. No. 10/123,484, filed Apr. 17, 2002, Gunaratnam.

* cited by examiner

RESPIRATORY MASK ASSEMBLY

CROSS REFERENCE TO RELATED APPLICATIONS

This application is a divisional application of U.S. application Ser. No. 09/498,705, filed Feb. 7, 2000 now U.S. Pat. No. 6,491,034, now allowed and related to the following co-pending applications: U.S. application Ser. No. 09/985,457, filed Nov. 2, 2001, pending and U.S. application Ser. No. 09/985,458, filed Nov. 2, 2001, pending the specifications and drawings of which are incorporated herein by reference.

BACKGROUND OF THE INVENTION

This invention relates to improvements in patient gas delivery apparatus of the kind used in the analysis and treatment of respiratory disorders. The invention will be described with particular reference to patient gas delivery apparatus used in the treatment of respiratory disorders such as Obstructive Sleep Apnea (OSA) but it is not intended to be limited thereto.

Patient gas delivery apparatus of the kind having a mask worn by a patient and a gas delivery conduit attached to the mask, is commonly used in the analysis and treatment of respiratory disorders. The gas conduit delivers a gas under pressure to the patient. It is necessary that the gas conduit is detachable from the mask to facilitate cleaning.

Patient gas delivery apparatus typically includes at a minimum, a gas delivery conduit and a nose or full face mask. In some cases it is a clinical requirement that additional components be included, such as means for $CO_2$ washout, for example, vents, anti-asphyxia valves and the like. In some cases, these additional components must be assembled in between the gas delivery conduit and the mask. Problems with prior art assemblies include:

(a) They may be inadvertently assembled without the additional components
(b) They may be incorrectly assembled, for example, incorrectly aligned
(c) During the course of treatment, the patient may inadvertently remove or dismantle the assembly and incorrectly reassemble it.

SUMMARY OF THE INVENTION

The present invention is directed towards solving or ameliorating one or more of these problems. The invention will be described with reference to a full face mask and an anti-asphyxia valve, though other forms of mask and additional components may be used.

In one form, the invention resides in a patient gas delivery apparatus including a mask adapted for communication with a patient's airways, a gas flow generator and gas delivery conduit means, further including an assembly connected in series between the conduit means and the mask, said assembly being formed in at least two parts connected by interengaging connecting means, said assembly further including means for connection to the mask, wherein connection of the assembly to the mask prevents disengagement of the interengaging connecting means such that said at least two parts of the assembly cannot separate whilst the assembly is connected to the mask.

In a further form of the invention, there is provided an assembly for connection in series between a gas delivery conduit means and a patient mask in a patient gas delivery apparatus, the assembly being formed in at least two parts connected by interengaging connecting means, said assembly further including means for connection to the mask, wherein connection of the assembly to the mask prevents disengagement of the interengaging connecting means such that said at least two parts of the assembly cannot separate whilst the assembly is connected to the mask.

Preferably, the means for connection to the mask includes locking means located on the inner side of the mask, that is in the region of the mask that lies adjacent the patient's face, such that the assembly cannot be disconnected from the mask until the mask has been substantially removed from the patient.

Preferably also, the interengaging means connecting the two parts of the assembly includes detent means on a first of the parts which releasably engage a second of the parts, the detents being held in an engaged position by the mask whilst the assembly is connected to the mask.

Desirably, the mask and conduit are not adapted for direct interconnection without the assembly.

In one preferred form of the invention, the assembly may form a housing for one or more internal components, for example a valve member or a flow sensor.

Further preferred embodiments of the invention will now be described by way of example only with reference to the accompanying drawings in which.

Figure 1:
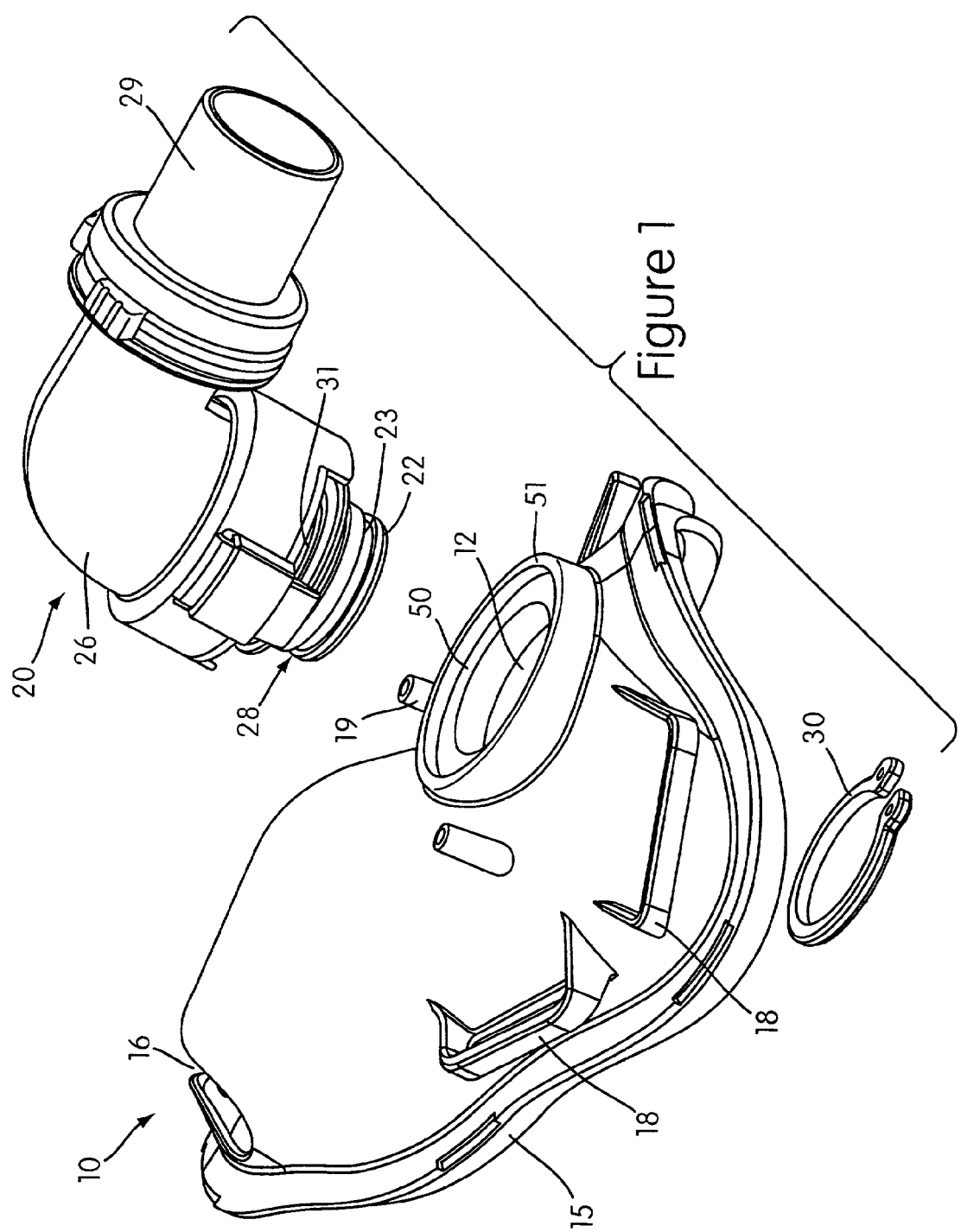
FIG. 1 is a perspective view showing the mask, anti-asphyxia valve housing and conduit connection assembly.

In FIG. 1 a mask frame is shown generally at 10. The mask is designed to be worn on a patient's face and is secured by means of straps (not shown) received by attachment points 18.

A conduit end assembly is shown generally at 20, including an elbow part 26 having at one end thereof a combined vent/connector piece 28. The elbow and vent/connector piece together form a housing for an anti-asphyxia valve or other internal components (not shown). At the other end of the elbow is a detachable swivel tube 29 for connection of the gas delivery conduit (not shown).

The mask 10 includes a circular aperture 12 sized to receive a mating portion 22 of the vent/connector piece 28. The mating portion 22 has an annular groove 23 formed therein that receives a locking means 30 in the form of a C-shaped clip attached after mating to the mask. The clip 30 has an outside diameter greater than the width of the aperture 12 and an inner diameter adapted to ensure a snug fit within the annular groove 23. The clip 30 is resilient and can expand sufficiently to allow the clip to be fitted into and removed from the groove 23. As shown in FIG. 1, the clip 30 is located onto the mating portion 22 on the inside of the mask 10. In this position, the clip 30 is inaccessible while the mask is being worn by a patient. Once the mating portion 22 of the vent/connector piece 28 has been inserted through the aperture 12 and the locking clip placed in the annular groove, the conduit end assembly 20 and the mask 10 cannot be separated without first removing the mask from the patient.

Figure 2:
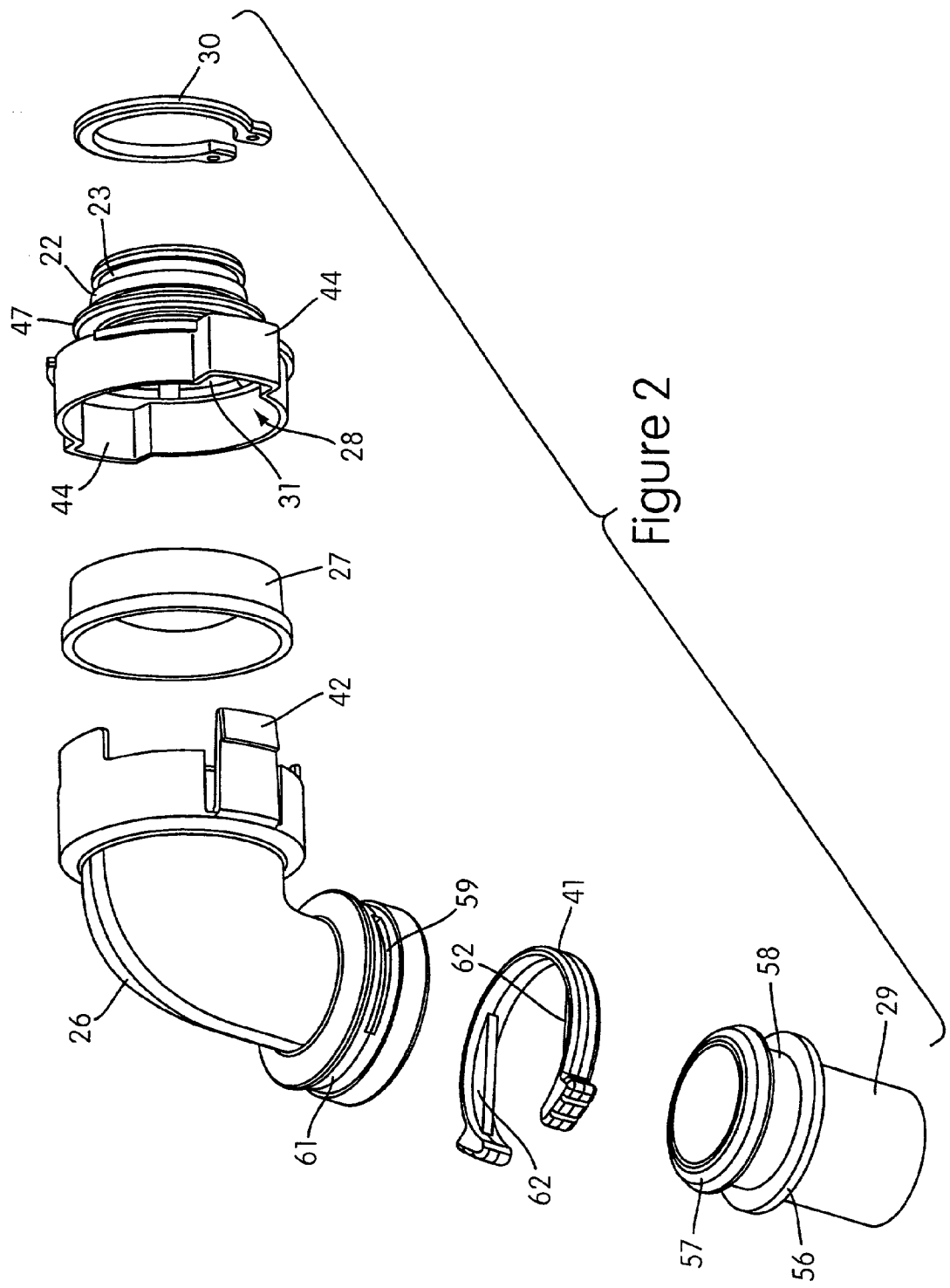
FIG. 2 is an exploded view of the anti-asphyxia valve and conduit connection assembly.

An exploded view of the anti-asphyxia valve and conduit connector assembly is shown in FIG. 2.

The end of the elbow 26 adjacent the mask 10 is fitted with an anti-asphyxia valve arrangement that provides an air passage to the patient in the event of failure of the gas delivery apparatus, consisting of a valve membrane 27 fitted into the end of elbow 26 and vents 31 in the vent/connector piece 28. During proper operation of the gas delivery system, the valve membrane remains in the orientation shown in FIG. 2, closing off the vents 31. In the event of a drop in pressure below a predetermined level, the valve membrane 27 flips to a reverse orientation, opening the vents 31. The construction and operation of the anti-asphyxia valve is described in more detail in the Applicant's Australian Patent Application No. 65527/99, the contents of which are incorporated herein by reference.

Resilient detents 42 on the elbow 26 pass through and engage behind slot-forming formations 44 in the vent/connector piece 28 to provide releasable engagement of the two parts.

The vent/connector piece has a collar 47 that abuts a corresponding surface of the mask 10 to limit the distance that the vent/connector piece can be inserted into the mask aperture 12 (FIG. 1). The corresponding surface is an annulus 50 having a protruding rim 51 the outer circumference of which preferably engages the inner surface of the detents 42 on insertion of the mating portion 22 into the aperture 12. This engagement prevents the detents from being pushed radially inwards sufficiently for the detents to disengage from behind the slot-forming formations 44, thus preventing the elbow 26 and vent/connector piece 28 from separating whilst still attached to the mask frame 11, for example during patient treatment. The result of this is that the anti-asphyxia valve arrangement cannot be disassembled without first removing the elbow and vent/connector piece assembly from the mask. However, once disconnected from the mask, the assembly may be readily separated for cleaning and then reassembled.

The other, distal end of elbow 26 has an enlarged diameter portion which receives the swivel tube 29, onto which a flexible gas conduit (not shown) may be fitted. The swivel tube 29 has a pair of flanges 56 and 57 defining an annular groove 58 therebetween. The end of swivel tube 29 is inserted into the elbow 26 until the end flange 57 abuts an inner surface (not shown) within elbow 26. In this position the annular groove 58 is at least partially aligned with an annular groove 61 in the exterior of the elbow, which receives a swivel clip 41.

The swivel clip 41 has an inner diameter only slightly greater than the diameter of the groove 61, to ensure a snug fit within the groove. The clip 41 is resilient to permit sufficient expansion for attachment and removal of the clip from the groove. The groove 61 has slots 59 which receive lugs 62 on the clip. These lugs rotatably engage in the groove 58 between flanges 56 and 57 of the swivel tube. The swivel tube arrangement thus acts as a rotatable coupling between the conduit and the elbow whilst allowing quick attachment and removal of the gas conduit from the elbow regardless of whether the assembly is attached to the mask at the time.

Figure 3:
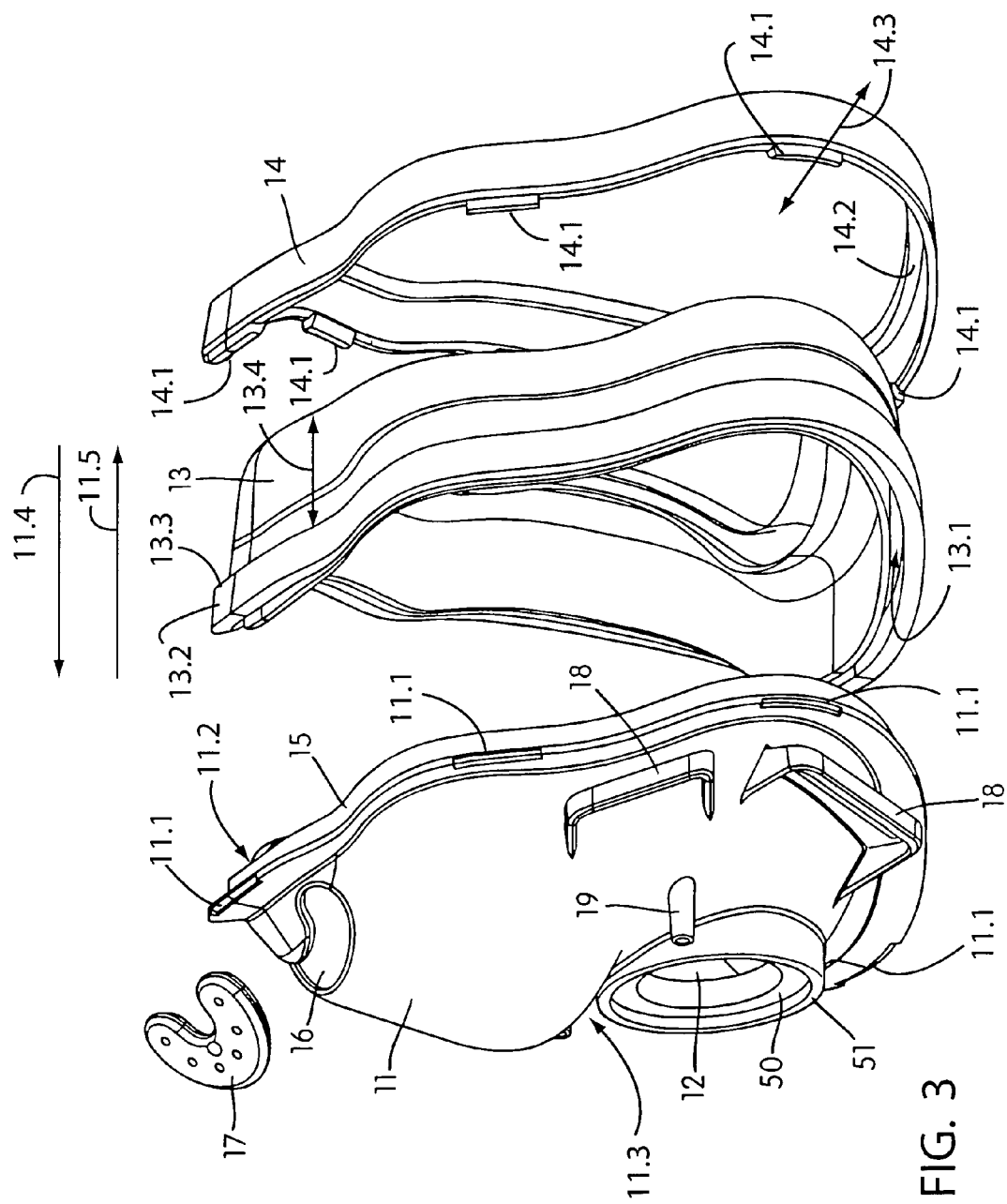
FIG. 3 is an exploded view of the mask assembly.

As shown in FIG. 3, the mask includes a mask frame 11, cushion 13 and cushion clip 14. The cushion is received on a rib 15 extending around the periphery of the mask frame 11. The cushion is held to the rib by the cushion clip 14. The mask frame includes attachment points 18 that receive straps (not shown) for attaching the mask to the patient, an aperture 16 for receiving an air vent 17, and measurement ports 19.

The mask frame 11 includes a plurality of recesses 11.1 that provide a first cooperating interlocking structure and the cushion clip 14 includes a plurality of tabs 14.1 that is equal to a number of recesses in the mask frame 11 and provides a second cooperating interlocking structure. The plurality of tabs 14.1 engage a respective recess 11.1 to secure the cushion clip 14 on the mask frame 11.

The mask assembly, in the example shown in FIG. 3, is a full face mask. As shown in FIG. 3, the frame includes top and bottom recesses, two left side recesses and two right side recesses (not shown). The cushion clip 14 includes corresponding top and bottom tabs 14.1 as well as two right side tabs (both shown) and two left side tabs (only one shown).

The mask cushion includes a groove 13.1 extending around the periphery thereof and the groove of the cushion receives the rib 15 of frame 11.

The cushion 13 includes an outwardly extending portion 13.2 that provides the groove 13.1 on one side thereof. An opposite side of the outwardly engaging portion 13.2 provides a shoulder 13.3 that engages a flange 14.2 on the cushion clip 14 to retain the cushion 13 on frame 11.

The cushion includes a rearwardly extending portion designated by reference number 13.4. The cushion serves to seal the mask assembly on the patient's face, and is structured to space the mask frame 11 from the patient's face.

The frame 11 includes a first side 11.2 structured to accommodate cushion 13, and a second side 11.3. The cushion clip 14 and frame 11 are configured to cooperate with one another such that the cushion clip 14 is selectively attachable to the frame 11 in a first direction 11.4 defined generally from the first side 11.2 to the second side 11.3 of the frame, to thereby secure the cushion 13 between the cushion clip 14 and the frame 11.

The cushion clip 14 and frame 11 are configured to cooperate with one another such that the cushion clip is selectively detachable from the frame 11 in a second direction 11.5, opposite to the first direction 11.4, defined generally from the second side 11.3 to the first side 11.2 of the frame 11, to thereby allow removal of the cushion 13 from frame 11.

Each tab 14.1 is resiliently movable in a third direction 14.3 that is substantially transverse to the first and second directions 11.4 and 11.5. Tab portions 14.1 move in the direction indicated by arrows 14.3 when the tab portions are snapped or flexed into place within recesses 11.1, and when they are removed therefrom.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein.

The invention claimed is:

1. A respiratory mask assembly for delivering breathable gas to a patient, comprising:
   a mask frame having a first cooperating interlocking structure;
   a cushion clip having a second cooperating interlocking structure and being selectively attachable to and detachable from the mask frame, the first and second cooperating interlocking structures interlocking with one another in a cooperating relationship to secure the cushion clip on the mask frame; and
   a mask cushion having an outer peripheral portion positioned between the mask frame and the cushion clip so as to retain the mask cushion on the mask frame,
   wherein the mask frame includes a plurality of recesses that provide the first cooperating interlocking structure and the cushion clip includes a plurality of tabs that is equal to a number of recesses in the mask frame and provides the second cooperating interlocking structure, the plurality of tabs engaging a respective recess to secure the cushion clip on the mask frame.

2. A respiratory mask assembly according to claim 1, wherein the mask assembly is a full-face mask and wherein the mask frame includes six recesses.

3. A respiratory mask assembly according to claim 1, wherein the mask frame includes a rib extending around the periphery thereof and the mask cushion includes a groove extending around the periphery thereof, the groove of the mask cushion receiving the rib of the mask frame.

4. A respiratory mask assembly according to claim 3, wherein the mask cushion includes an outwardly extending portion that provides the groove on one side thereof, an opposite side of the outwardly extending portion providing a shoulder that engages a flange on the cushion clip to retain the mask cushion on the mask frame.

5. A respiratory mask assembly according to claim 1, wherein the mask cushion includes a rearwardly extending portion structured to space the mask frame from the patient's face.

6. A respiratory mask assembly according to claim 1, wherein the frame includes a first side structured to accommodate the cushion, and a second side, opposite the first side, and wherein the cushion clip and frame are configured to cooperate with one another such that the cushion clip is selectively attachable to the frame in a first direction defined generally from the first side to the second side of the frame, to thereby secure the cushion between the cushion clip and the frame.

7. A respiratory mask assembly according to claim 6, wherein the cushion clip and frame are configured to cooperate with one another such that the cushion clip is selectively detachable from the frame in a second direction, opposite the first direction, defined generally from the second side to the first side of the frame, to thereby allow removal of the cushion from the frame.

8. A respiratory mask assembly according to claim 1, wherein the cushion clip is selectively attachable to and detachable from the cushion.

9. A respiratory mask assembly for delivering breathable gas to a patient, comprising:
   a mask frame having a first cooperating interlocking structure;
   a cushion clip having a second cooperating interlocking structure and being selectively attachable to and detachable from the mask frame, the first and second cooperating interlocking structures interlocking with one another in a cooperating relationship to secure the cushion clip on the mask frame; and
   a mask cushion having a portion positioned between the mask frame and the cushion clip;
   wherein the mask frame includes a plurality of recesses that provide the first cooperating interlocking structure and the cushion clip includes a plurality of tabs that is equal to a number of recesses in the mask frame and provides the second cooperating interlocking structure, the plurality of tabs engaging a respective recess to secure the cushion clip on the mask frame.

10. A respiratory mask assembly according to claim 9, wherein the frame includes a first side structured to accommodate the cushion, and a second side, opposite the first side, and wherein the cushion clip and frame are configured to cooperate with one another such that the cushion clip is selectively attachable to the frame in a first direction defined generally from the first side to the second side of the frame, to thereby secure the cushion between the cushion clip and the frame.

11. A respiratory mask assembly according to claim 10, wherein the cushion clip and frame are configured to cooperate with one another such that the cushion clip is selectively detachable from the frame in a second direction, opposite the first direction, defined generally from the second side to the first side of the frame, to thereby allow removal of the cushion from the frame.

12. A respiratory mask assembly according to claim 7, wherein the first and second interlocking structures are engagable when the cushion clip is moved in a first direction defined generally from a first side of the frame that supports the cushion towards a second side of the frame opposite the first side, to thereby secure the cushion between the cushion clip and the frame.

13. A respiratory mask assembly according to claim 12, wherein the first and second interlocking structures are disengagable when the cushion clip is moved in a second direction defined generally from the second side towards the first side of the frame, to thereby allow removal of the cushion from the frame.

14. A respiratory mask assembly according to claim 13, wherein each said tab is resiliently movable in a third direction that is substantially transverse to the first and second directions, upon selective engagement and disengagement between the cushion clip and the frame.

15. A respiratory mask assembly for delivering breathable gas to a patient, comprising:
   a mask frame having a first cooperating interlocking structure;
   a cushion clip having a second cooperating interlocking structure and being selectively attachable to and detachable from the mask frame, the first and second cooperating interlocking structures interlocking with one another in a cooperating relationship to secure the cushion clip on the mask frame; and
   a mask cushion provided to the mask frame,
   wherein the mask frame includes at least a first recess positioned along a first side of the frame and a second recess positioned along a second side of the frame, the first and second recesses providing the first cooperating interlocking structure, and wherein the cushion clip includes at least a first tab positioned along a first side of the cushion clip and a second tab positioned along a second side of the cushion clip, the first and second tabs providing the second cooperating interlocking structure, the first and second tabs being engagable with the first and second recesses, respectively, to secure the cushion clip on the mask frame.

16. A respiratory mask assembly according to claim 15, wherein the frame includes a first side structured to accommodate the cushion, and a second side, opposite the first side, and wherein the cushion clip and frame are configured to cooperate with one another such that the cushion clip is selectively attachable to the frame in a first direction defined generally from the first side to the second side of the frame, to thereby secure the cushion between the cushion clip and the frame.

17. A respiratory mask assembly according to claim 16, wherein the cushion clip and frame are configured to cooperate with one another such that the cushion clip is selectively detachable from the frame in a second direction, opposite the first direction, defined generally from the second side to the first side of the frame, to thereby allow removal of the cushion from the frame.

18. A respiratory mask assembly according to claim 15, wherein the mask frame includes a rib extending around the periphery thereof and the mask cushion includes a groove extending around the periphery thereof, the groove of the mask cushion receiving the rib of the mask frame.

19. A respiratory mask assembly according to claim 18, wherein the mask cushion includes an outwardly extending portion that provides the groove on one side thereof, an opposite side of the outwardly extending portion providing a shoulder that engages a flange on the cushion clip to retain the mask cushion on the mask frame.

20. A respiratory mask assembly for delivering breathable gas to a patient, comprising:

a mask frame having a first cooperating interlocking structure;

a cushion clip having a second cooperating interlocking structure and being selectively attachable to and detachable from the mask frame, the first and second cooperating interlocking structures interlocking with one another in a cooperating relationship to secure the cushion clip on the mask frame; and a mask cushion having an outer peripheral portion positioned between the mask frame and the cushion clip so as to retain the mask cushion on the mask frame, wherein the cushion clip is selectively attachable to and detachable from the cushion, and wherein the mask frame includes a rib extending around the periphery thereof and the mask cushion includes a groove extending around the periphery thereof, the groove of the mask cushion receiving the rib of the mask frame.

21. A respiratory mask assembly according to claim 20, wherein the mask cushion includes an outwardly extending portion that provides the groove on one side thereof, an opposite side of the outwardly extending portion providing a shoulder that engages a flange on the cushion clip to retain the mask cushion on the mask frame.

* * * * *